(12) United States Patent
Dettinger et al.

(10) Patent No.: US 11,120,911 B2
(45) Date of Patent: Sep. 14, 2021

(54) DYNAMICALLY ADAPTIVE CARE PLANS

(71) Applicant: PREVENTICE, INC., Rochester, MN (US)

(72) Inventors: Richard D. Dettinger, Rochester, MN (US); Richard M. Smith, Oronoco, MN (US); Scott J. Burrichter, Rochester, MN (US)

(73) Assignee: PREVENTICE SOLUTIONS, INC., Rochester, MN (US)

( * ) Notice: Subject to any disclaimer, the term of this patent is extended or adjusted under 35 U.S.C. 154(b) by 887 days.

(21) Appl. No.: 14/490,443

(22) Filed: Sep. 18, 2014

(65) Prior Publication Data

US 2016/0085927 A1    Mar. 24, 2016

(51) Int. Cl.
*G16H 50/20* (2018.01)
*G06Q 10/00* (2012.01)
*G06F 19/00* (2018.01)

(52) U.S. Cl.
CPC ............. *G16H 50/20* (2018.01); *G06F 19/00* (2013.01); *G06Q 10/00* (2013.01)

(58) Field of Classification Search
CPC .. G06Q 10/00; G06Q 50/24; G06Q 50/22–24; G06F 3/04847; G06F 19/3418; A61B 5/02427; A61B 5/14539; A01G 9/02; G16H 50/20
See application file for complete search history.

(56) References Cited

U.S. PATENT DOCUMENTS

| | | | | |
|---|---|---|---|---|
| 2006/0154642 | A1* | 7/2006 | Scanned, Jr. | G08B 7/066 455/404.1 |
| 2007/0033072 | A1* | 2/2007 | Bildirici | G09B 19/00 705/3 |
| 2012/0041788 | A1* | 2/2012 | Wons | G06Q 10/06 705/3 |
| 2012/0101847 | A1* | 4/2012 | Johnson | G06Q 30/00 705/3 |

(Continued)

FOREIGN PATENT DOCUMENTS

WO    2014/116968 A1    7/2014

OTHER PUBLICATIONS

International Search Report and Written Opinion—PCT/US2015/050569, dated Nov. 4, 2015.

*Primary Examiner* — Robert W Morgan
*Assistant Examiner* — Edward B Winston, III
(74) *Attorney, Agent, or Firm* — Patterson + Sheridan, LLP (57) ABSTRACT

Embodiments presented herein provide a dynamically adaptive care plan. More specifically, embodiments presented herein describe techniques for modifying a care plan assigned to a patient based on data observed from the patient. According to one embodiment of the present disclosure, data corresponding to one or more types of biometric data for the patient is received. One or more reported symptoms for the patient is received. The care plan includes one or more conditions corresponding to the one or more reported symptoms. Upon determining that at least one of the received data satisfy at least one of the biometric thresholds and the one or more reported symptoms satisfy at least one of the conditions, an event rule for modifying the care plan is identified. The care plan is modified based on the event rule.

20 Claims, 6 Drawing Sheets

(56) References Cited

U.S. PATENT DOCUMENTS

| | | | | |
|---|---|---|---|---|
| 2013/0179178 A1* | 7/2013 | Vemireddy | ............ | G06Q 10/00 |
| | | | | 705/2 |
| 2014/0201627 A1* | 7/2014 | Freeman | ............... | G06F 3/0481 |
| | | | | 715/704 |
| 2014/0222454 A1* | 8/2014 | Duffy | ..................... | G16H 10/20 |
| | | | | 705/2 |
| 2014/0288435 A1* | 9/2014 | Richards | ............ | A61B 5/14539 |
| | | | | 600/479 |
| 2015/0359489 A1* | 12/2015 | Baudenbacher | ....... | G16H 40/67 |
| | | | | 600/300 |

\* cited by examiner

| State 350 | Threshold trigger 355 | Event rule 360 |
|---|---|---|
| A | Non-active for X duration, heart rate > Y | Add task: Deep breathing exercises for 5 minutes; Prompt for symptoms |
| A1 | Non-active for Z duration, heart rate > Y, reported symptoms: stress | Add task: Deep breathing exercises for 10 minutes |
| A2 | Heart rate > Y for W duration | Add task: Take medication |
| A3 | Heart rate > Y for V duration | Contact care provider |
| B | Heart rate > Y, reported symptom: chest pains | Contact care provider |
| C | Heart rate > T | Contact care provider |
| ... | ... | ... |

DYNAMICALLY ADAPTIVE CARE PLANS

BACKGROUND

Field

Embodiments of the present disclosure generally relate to health care. More specifically, embodiments relate to techniques for a health care plan that may adapt to observation data obtained from a patient.

Description of the Related Art

In the health care field, a care plan is a set of tasks provided by a health care practitioner (e.g., a doctor) to a patient. Historically, such a care plan is a written document that provides directions and routines for the patient to follow to manage certain health conditions. The care plan may include a set of tasks (e.g., exercise for a given duration) for the patient to perform, content that educates the patient about a diagnosed condition (e.g., brochures describing the diagnosed condition), and logs for the patient to periodically record information in (e.g., weight, blood pressure, etc.). As an example, a doctor might create a care plan for a patient with hypertension that includes several brochures describing hypertension and hypertension treatment and assigned tasks such as walking on a treadmill for thirty minutes each morning, drinking a glass of water every three hours, and recording blood pressure at the end of each day. Thus, as part of the treatment of the condition, the patient is expected to adhere to the tasks listed in the care plan and to then follow up with the doctor in a subsequent appointment to assess the patient's progress.

The current care plan approach has several shortcomings. For instance, a care plan for a particular condition is often tailored towards the condition itself, without considering relevant details about a patient. Typically, once a doctor has diagnosed a patient with a particular condition, the doctor prints out a "one size fits all" care plan for the individual that instructs the individual on how to manage the condition. Although such a care plan may have advantages, patients may still respond differently to the care plan. As a result, the care plan may be less effective for some than it is for others. Further, the doctor often has no way of determining the patient's adherence to the care plan until a follow-up appointment. Currently, to address this concern, care provider employs call centers to contact the patient periodically and determine whether the patient is following the care plan, but such an approach is costly and further exposes a patient's condition to more individuals than necessary.

SUMMARY

One embodiment of the present disclosure includes a method for modifying a care plan assigned to a patient in response to data observed from the patient. The method generally includes receiving data corresponding to one or more types of biometric data for the patient. The care plan includes one or more biometric thresholds corresponding to the one or more types of biometric data. The method also includes receiving one or more reported symptoms for the patient. The care plan includes one or more conditions corresponding to the one or more reported symptoms. Upon determining that at least one of the received data satisfy at least one of the biometric thresholds and the one or more reported symptoms satisfy at least one of the one or more conditions, an event rule for modifying the care plan based on the received data and the one or more reported symptoms is identified. The care plan is modified based on the event rule.

Still another embodiment includes a computer-readable storage medium storing instructions, which, when executed on a processor, perform an operation for modifying a care plan assigned to a patient in response to data observed from the patient. The operation itself includes receiving data corresponding to one or more types of biometric data for the patient. The care plan includes one or more biometric thresholds corresponding to the one or more types of biometric data. The operation also includes receiving one or more reported symptoms for the patient. The care plan includes one or more conditions corresponding to the one or more reported symptoms. Upon determining that at least one of the received data satisfy at least one of the biometric thresholds and the one or more reported symptoms satisfy at least one of the one or more conditions, an event rule for modifying the care plan based on the received data and the one or more reported symptoms is identified. The care plan is modified based on the event rule.

Still another embodiment includes a system having a processor and a memory a memory storing one or more application programs configured to perform an operation for modifying a care plan assigned to a patient in response to data observed from the patient. The operation itself includes receiving data corresponding to one or more types of biometric data for the patient. The care plan includes one or more biometric thresholds corresponding to the one or more types of biometric data. The operation also includes receiving one or more reported symptoms for the patient. The care plan includes one or more conditions corresponding to the one or more reported symptoms. Upon determining that at least one of the received data satisfy at least one of the biometric thresholds and the one or more reported symptoms satisfy at least one of the one or more conditions, an event rule for modifying the care plan based on the received data and the one or more reported symptoms is identified. The care plan is modified based on the event rule.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Current approaches for providing a care plan to a patient are rigid. For example, in many cases, a physician who has diagnosed a particular condition in a patient may provide the patient with a generalized care plan commonly used to address that condition. Frequently, these generalized care plans are pre-printed documents that are not tailored to any particular patient but rather generally address the diagnosed medical condition. However, such a "one size fits all" care plan typically does not account for individual patients reacting differently to the care plan. For example, a care plan targeted at treating hypertension may include tasks for performing a type of daily exercise for a specific duration, such as walking on a treadmill for thirty minutes. Although such an exercise may be effective in easing one patient's high blood pressure, another patient may require more (or different) activity for the same improvement. Thus, current care plan solutions may be beneficial for some but ineffective or even adverse to others.

Embodiments presented herein describe techniques for dynamically modifying a care plan for a particular patient in response to received data associated with the patient. In one embodiment, a care platform allows a physician to design an adaptive care plan tailored specifically for an individual patient. The care plan may include multiple care plan protocols, with each of the care plan protocols addressing a respective medical condition the patient has been diagnosed with. Generally, a care plan protocol describes the treatment of a particular medical condition. For instance, a care plan could specify a set of specific tasks that a patient follows to manage a particular condition and could divide the tasks by phases and schedules. The care plan protocol may divide the tasks by phases and schedules. Further, a care plan protocol may be available for a variety of conditions, such as congestive heart failure, diabetes, sprained ankle, etc.

In addition, the care protocol may specify metrics that the care platform monitors during the patient's treatment, thresholds to detect for each metric and remedial actions to be taken in response to detecting such thresholds. One example metric is blood pressure. The blood pressure metric may be associated with thresholds indicating values and conditions in which the care platform performs some action in response to detecting such values and conditions, e.g., sending instructions to the patient to rest for a given period of time. Further, the care protocol may provide the patient with resources to educate the patient about a diagnosed condition, treatment, and the like (e.g., instructional videos, articles, etc.). The care platform provides a template for each care plan protocol. The care platform may consolidate the configured care plan protocols into one overall care plan for the patient.

Once created, the care platform may transmit the care plan to an application in a device owned by the patient, e.g., a smart phone or tablet device. Though the device, the patient may access the care plan and understand the tasks to perform. Further, the application may receive information from various sensors that monitor patient activity (e.g., heart rate, weight, blood pressure). In addition, the mobile application may prompt the patient to report symptoms experienced while adhering to the care plan. The application can record the information to the care plan and relay information to the care platform. As a result, the physician can monitor the patient's adherence to the care plan.

Likewise, the care platform may monitor the patient's adherence to the care plan based on sensor data and reported symptoms received (e.g., from the mobile application) and, in response, automatically modify the care plan in the event that observed patient biometrics and/or reported symptoms satisfies a corresponding threshold condition. If a threshold condition is satisfied, the care platform may modify the care plan based on an event rule associated with the threshold condition. Thereafter, the care platform continues to obtain sensor data (and reported symptoms) from the patient after the modification. The care platform determines whether the metrics have improved based on the changes made to the care plan.

For example, assume that a care plan for a given patient includes a threshold for a patient's blood pressure, e.g., specifying that over a given day, the patient's systolic blood pressure should not exceed 145 mmHg. If sensor data retrieved from the patient indicates that the blood pressure crosses the threshold, the care platform may insert a task instructing the patient to perform some action to lower the blood pressure, such as increase medication or perform breathing exercises for a period of time. Further, the care platform may include an additional blood pressure threshold, e.g., higher than the original threshold. The care platform notifies the patient of the change (i.e., through the mobile application) and continues to monitor the sensor data sent by the patient. As another example, the care platform could include another condition that specifies that if the patient's systolic blood pressure exceeds 135 mmHg and the patient reports feeling the symptom of dizziness, the care platform should perform a treatment regimen aimed at reducing the patient's blood pressure, e.g., instructing the patient to rest and perform breathing exercises. The care platform may continue to add or change tasks aimed at achieving a desired outcome.

Continuing the previous example, assume the care platform receives sensor data indicating that the patient's metrics are not improving, e.g., the blood pressure has exceeded a second threshold, then the care platform may insert additional tasks and thresholds to the care plan. In addition, the care platform may alert a care provider or emergency services if the modifications to the care plan eventually prove to be ineffective.

Figure 1:
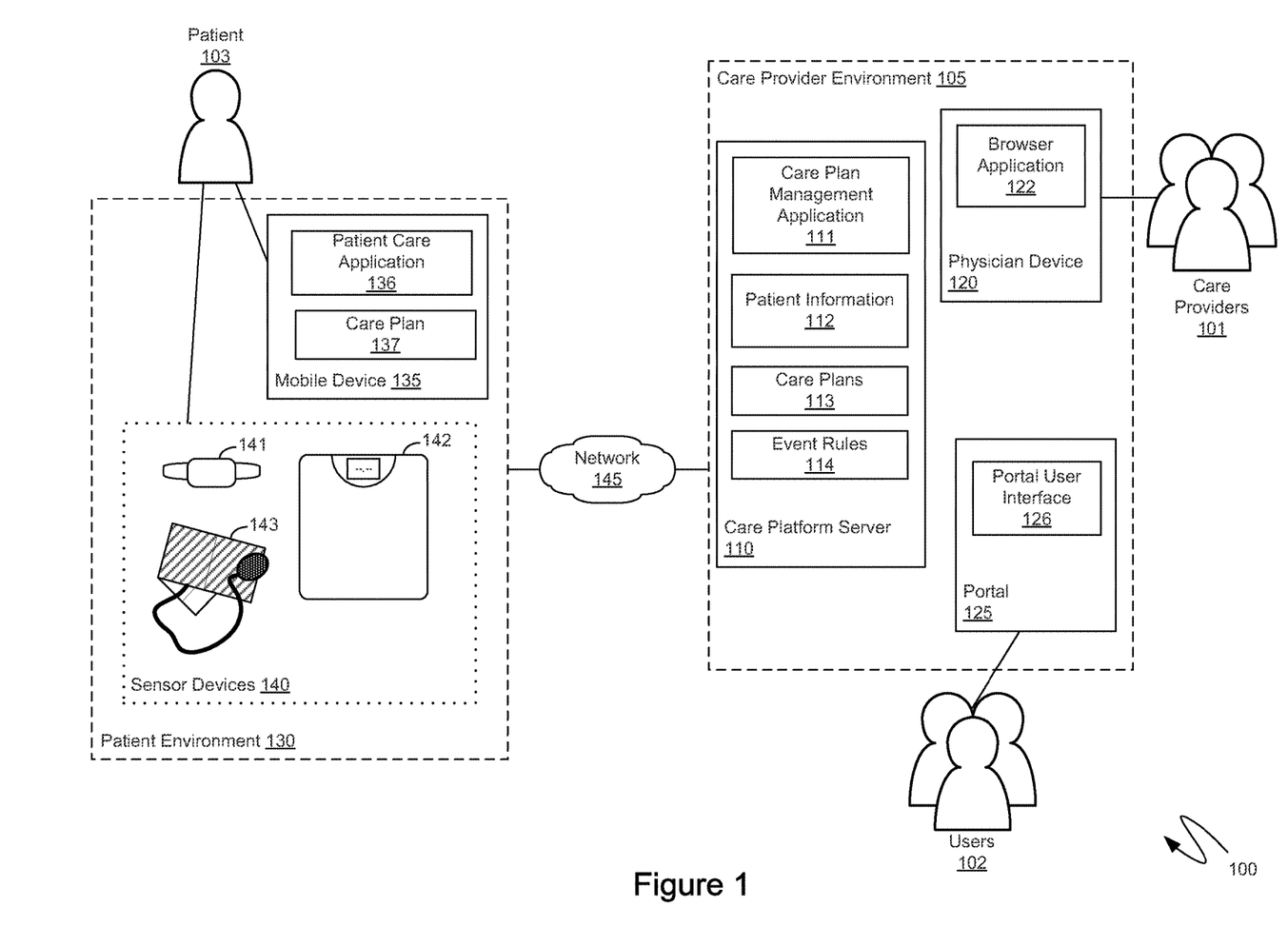
FIG. 1 illustrates an example computing environment, according to one embodiment.

FIG. 1 illustrates an example computing environment 100, according to one embodiment. As shown, the computing environment 100 may include a care provider environment 105 and a patient environment 130, each connected to one another via a network 145. The environments 105 and 130 allow a patient 103 to communicate with a care provider 101 (e.g., a physician).

The care provider environment 105 includes a care platform server 110, a physician device 120, and a portal 125. Each of the care platform server 110, physician device 120, and portal 125 may be a physical computing system or may be a virtual computer instance (e.g., executing in a cloud computing platform). A care provider 101 may use the physician device 120 to access (e.g., via a browser application 122) a portal user interface 126 hosted by the portal 125. The portal user interface 126 itself provides users 102 (e.g., the care providers 101) with access to the care platform server 110.

The care platform server 110 includes various applications and data that allow a care provider 101 to manage a care plan for a patient 103. As shown, the care platform server 110 includes a care plan management application 111, patient information 112, care plans 113, and event rules 114.

A care plan 113 may include one or more care protocols with each of the care protocols relating to a respective medical condition the patient has been diagnosed with. A care protocol is a set of tasks that a patient 103 follows to manage a certain condition, metrics that the care plan management application 111 monitors, objectives for the patient, and the like. For instance, a care protocol may target recovery from a heart attack. Another care protocol may treat diabetes. Tasks associated with a care protocol may include steps such as exercising for a specified duration or taking medication at a certain time of day. Other tasks may prompt the user to report current symptoms to the care platform server 111. Further, each care plan protocol may be divided into different phases. The phases may represent different stages of care for a particular condition, e.g., a recovery phase, a maintenance phase, etc.

For example, a care protocol for weight management may include several phases. A patient 103 may begin the care protocol at a weight loss phase, where tasks may include performing strenuous exercises frequently, and where thresholds may specify further actions that the care plan management application 111 takes if the patient 103 loses X amount of weight or gains Y amount of weight. For example, if the metrics indicate that the patient 103 gained Y amount of weight after a period at which the patient 103 had a Z average activity level, the care plan management application 111 may instruct the patient 103 to watch an educational video in response. Continuing the example, if the patient 103 loses X amount of weight during a given period, the care plan management application 111 may transition the care protocol to a weight maintenance phase, where tasks may include exercises that assist the patient 103 in maintaining the weight.

Each care plan protocol may also include thresholds associated with monitored metrics and could further specify an action(s) to be taken responsive to an observation threshold being satisfied. The care platform server 110 may monitor the adherence of a patient 103 through various sensor devices 140 that can measure heart rate, weight, blood pressure, and the like. The care platform server 110 may take action (e.g., specified in an event rule 114, further described below) if one of the metrics exceeds a corresponding threshold, e.g., if a patient 103 gains 1.5 pounds after a day, the platform server 110 may modify the care plan 113.

The care plan management application 111 generates a care plan 113 for a patient 103 based on care plan protocols selected and customized by the care provider 101. The care plan management application 111 may store the care plan 113 on the care platform server 110. Further, the care plan management application 111 transmits the care plan 113 to a mobile device 135 (e.g., to a patient care application 136 executing on the mobile device 135) of the patient 103. The patient 103 views the care plan (shown as care plan 137) on the mobile device through the patient care application 136. Doing so allows the patient 103 to understand tasks needed to adhere to the platform.

Moreover, the mobile device 135, upon receiving the care plan, could configure one or more sensor devices 140 to monitor one or more patient metrics as specified by the care plan. For example, the mobile device 135 could configure logic on a heart rate monitor device worn by the patient to monitor the patient's heart rate and to detect when the patient's heart rate exceeds a threshold number of beats per minute specified within the care plan. The heart rate monitor device, upon detecting that the threshold condition has been satisfied, could transmit an alert to the mobile device 135, which could in turn perform an action as specified by the care plan. For example, the mobile device 135, upon receiving the alert, could display a notification to the patient, informing the patient that his heart rate is elevated and instructing the patient to sit down and rest for a period of time. As another example, the mobile device 135 could generate a notification to the care plan management application 111, informing the care plan management application 111 that the patient's heart rate exceeds the threshold amount of beats per minute.

The patient care application 136 may display information related to the care plan 137, such as phases, tasks, and other information about conditions targeted for treatment by the care plan 137. When the patient 103 performs a task, the patient 103 records progress in the patient care application 136. The patient care application 136 relays this information to the care plan management application 111. Doing so allows the care provider 101 to monitor the body metrics of the patient 103 and adherence to the care plan. Further, depending on how the patient 103 responds to the care plan 137, the care plan management application 111 may adjust certain tasks.

As stated, sensor devices 140 may send biometric information to the patient care application 136. As shown, such sensor devices 140 may include an adhesive body sensor 141, a weighing scale 142, and a blood pressure cuff 143. More generally, any device capable of collecting data associated with a patient may be used, consistent with the present disclosure. Each of the sensor devices 140 may capture different biometrics of the patient 103. For example, when applied to the body of patient 103, the adhesive body sensor 141 captures biometric data (e.g., heart rate) in real-time. In addition, each of the sensor devices 140 may be configured to transmit the biometrics electronically to the patient care application 136. In turn, the patient care application 136 sends the captured biometrics to the care plan management application 111.

In one embodiment, the care plan management application 111 modifies a care plan 113 assigned to a patient 103 based on the biometric data captured by the sensor devices 140 and based on information reported (e.g., via an interface of the mobile application) by the patient. Specifically, the care plan management application 111 evaluates the biometric data and reported patient information against conditions specified in the care plan 113. If the observed biometrics and/or reported symptoms satisfy a given condition, the care plan management application 111 may trigger a corresponding event rule 114. The event rules 114 specify actions that the care plan management application 111 takes in response to a given condition being satisfied. For instance, an event rule 114 may specify new tasks and expected threshold conditions to insert into the care plan 113. Event rules 114 may also specify existing tasks and threshold conditions to change or remove from the care plan 113.

In addition, the care plan management application 111 may adjust the care plan 113 based on compliance by the patient 103. For example, the patient 103 could be assigned the task of reading particular educational content on the patient care application 136 every morning as part of the administration of the care plan 137. If the care plan management application 111 detects that the patient 103 is infrequently completing the assigned task, the care plan management application 111 could alter the care plan 113 to provide the educational content through a different medium. For instance, the care plan management application 111 could alter the care plan 111 such that the patient is assigned to watch an educational video on the same topic as the written educational content. Doing so allows the care plan 113 to be adjusted to suit the individual preferences of the patient 103 while also ensuring that the patient 103 completes the assigned tasks specified in the care plan 113.

New or modified conditions may also be associated with a corresponding event rule 114. A threshold and a corresponding event rule 114 may reflect a given state of health of the patient 113 based on the observed biometric data and reported symptoms. Each task associated with a new state is aimed towards orienting the biometrics observed in a patient 103 towards a desired result and/or eliminating symptoms experienced by the patient 103. Each state may branch off into other states in response to subsequently observed sensor data. Eventually, if the subsequently observed metrics do not indicate improvement, the care plan management application 111 may reach an end state, where the corresponding event rule 114 specifies that action by a care provider 101 or emergency services is required. In such an event, the care plan management application 111 can alert a care provider 101 or emergency services.

In one embodiment, the event rules 114 are created in accordance with patient information 112 and policies of the care provider 101. Patient information 112 may include treatment history of the patient 103, such as medications previously prescribed and whether the medications had a beneficial or adverse effect towards the patient. The care plan management application 111 may add tasks known to be effective in treating the patient, based on the patient information 112. Conversely, the care plan management application 111 may avoid adding tasks known to be adverse to the patient's health. For example, the patient information 112 could specify that the patient 103 has been assigned the task of performing lunges in the past as part of an exercise routine and has indicated (e.g., using an interface of the patient care application 136 on mobile device 135) that this exercise caused the symptom of knee pain for the patient 103. Accordingly, if the care plan 137 enters a weight loss phase during which additional exercises are prescribed, the care plan management application 111 could avoid adding lunges to the care plan 137 based on the patient's previously reported symptoms from this exercise as specified by the patient information 112. Further, the care plan management application 111 may add data (e.g., tasks and thresholds added, observed patient biometrics) to the patient information 112 each time the application 111 modifies the care plan 113.

Figure 2:
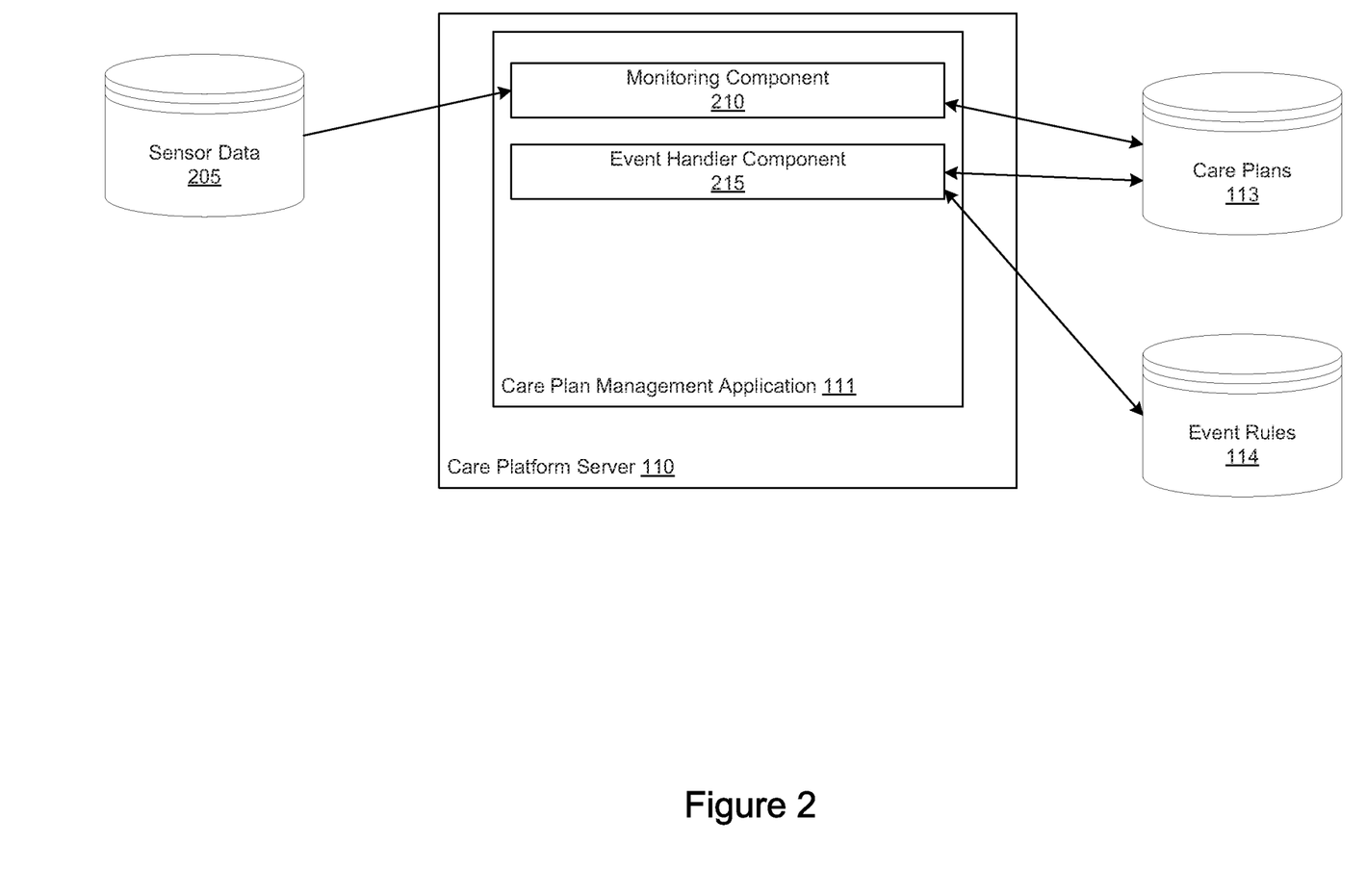
FIG. 2 further illustrates the care plan management application described in FIG. 1, according to one embodiment.

FIG. 2 further illustrates the care platform server 115, according to one embodiment. As stated, the care plan management application 111 modifies a care plan 113 based on sensor data 205 retrieved from a patient 103. As shown, the care plan management application 111 further includes a monitoring component 210 and an event handler component 215. The monitoring component 210 receives sensor data 205, i.e., biometric information of a patient 103, from the patient care application 136. The monitoring component 210 records the sensor data 205 to the care plan 113 assigned to the patient 103. Further, monitoring component 210 evaluates the sensor data 205 against thresholds specified in the care plan 113. Doing so allows the monitoring component 210 to detect any deviations from an expected state of the patient 103. If the sensor data 205 exceeds any of the thresholds, the monitoring component 210 relays the metrics and threshold data to the event handler component 215.

For example, assume that a care plan 113 assigned to a patient 103 is targeted towards recovery from congestive heart failure. Also assume that the care plan 113 specifies a threshold for the heart rate of the patient 103 that is triggered when the patient 103 is sedentary but the heart rate is over a given value. The patient 103 wears an adhesive body sensor 141, which relays the patient's heart rate as sensor data 205 to the patient care application 136. In turn, the patient care application 136 sends the sensor data 205 to the monitoring component 210. The monitoring component 210 may evaluate metrics such as the patient's heart rate and whether the patient is active against the threshold. If the observed metrics trigger the threshold, then the monitoring component 210 sends the metrics and threshold data to the event handler component 215.

In one embodiment, the event handler component 215 identifies an event rule 114 corresponding to the triggered threshold. As stated, event rules 114 specify a particular action to be performed in the event that the observed data exceeds a threshold. Such actions may include adding or removing tasks and thresholds to the care plan 113. The event handler component 215 performs the action specified in the event rule 114.

Continuing the previous example, an event rule 114 corresponding to the triggered threshold may specify to the event handler component 215 to insert additional tasks into the care plan 113 that the patient 103 should follow to reduce heart rate. For example, a task may instruct the patient 103 to perform deep breathing exercises in solitude for a given duration. Another task may instruct the patient 103 to increase dosage of a heart rate-lowering medication. The event handler component 215 may also insert additional thresholds to the care plan 113 used to subsequently determine whether the patient's heart rate continues to increase despite adherence to the added tasks. As stated, such thresholds may also be associated with event rules 114 specifying what actions to take in the event that newly observed metrics trigger the added thresholds.

Generally, each pair of threshold triggers and event rules 114 may be expressed as a state of a care plan 113. When incoming observation data triggers a threshold corresponding to a particular state, the care plan management application 111 transitions the care plan 113 to that state. An improvement reflected in newly observed biometrics of the patient 103 may allow the care plan management application 111 to revert to a previous state. Tasks added in response to new thresholds being triggered are generally aimed at reverting the care plan 113 to a previous state.

Figure 3A:
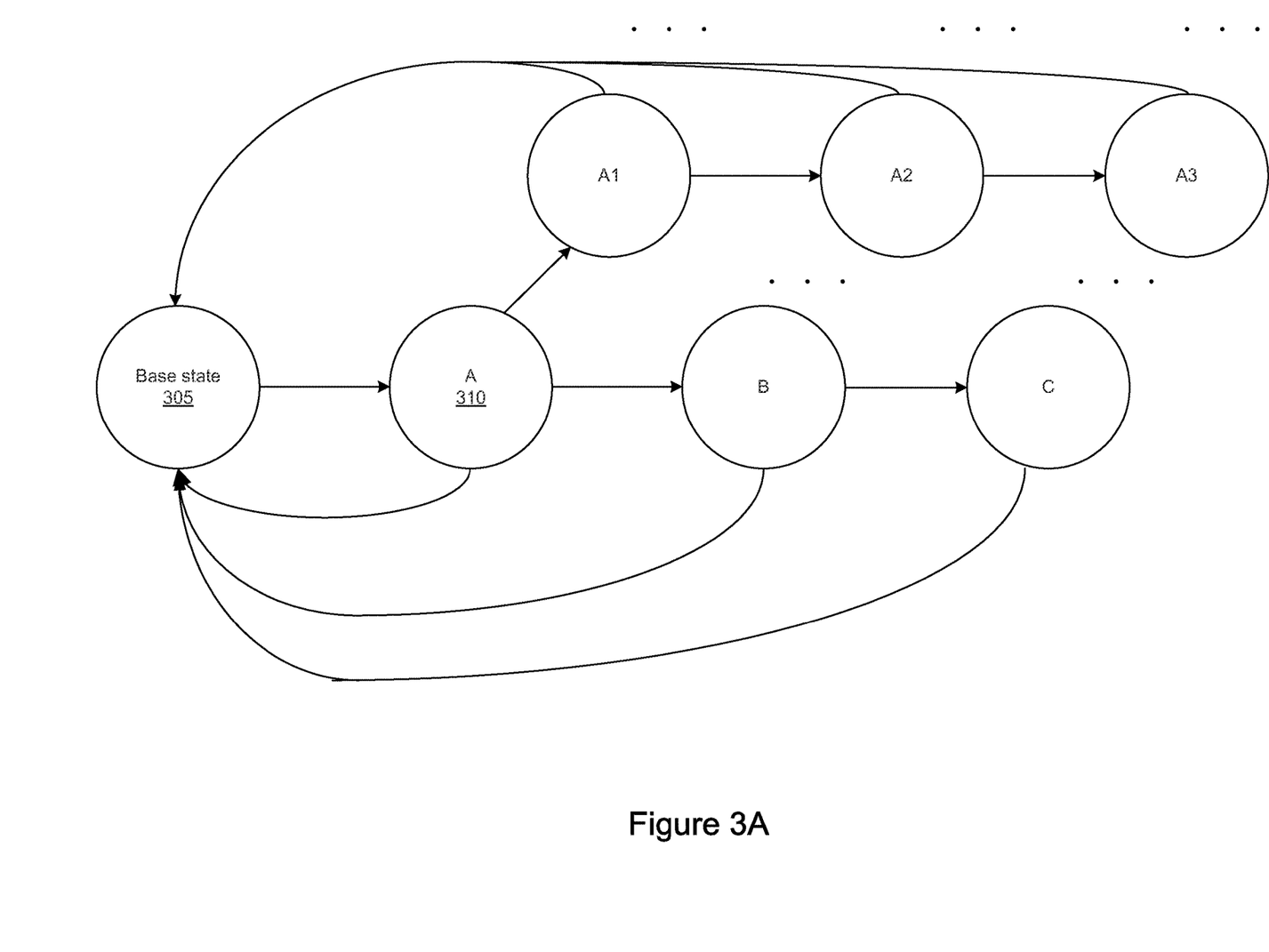
FIG. 3A illustrates example progressions through care plan states, according to one embodiment.

FIG. 3A illustrates example progressions through care plan states, according to one embodiment. When created, a care plan 113 assigned to a patient 103 begins at a base state 305. As the care plan management application 111 observes sensor data, the care plan 113 may transition into different states if the biometrics observed in the sensor data trigger thresholds associated with the different states. For example, the care plan 113 may transition from the base state 305 to a state A 310 if thresholds associated with state A 310 are triggered.

Illustratively, the different states may branch off from a current state based on the observed biometrics. For example, depending on subsequently observed biometrics, the state A 310 may transition into either a state A1 or a state B. Each subsequent state may branch off into multiple states. Further, as described, if subsequently observed biometrics indicate an improvement, i.e., the biometrics fall below a previously triggered threshold, then the care plan 113 may revert to a previous state.

Figure 3B:
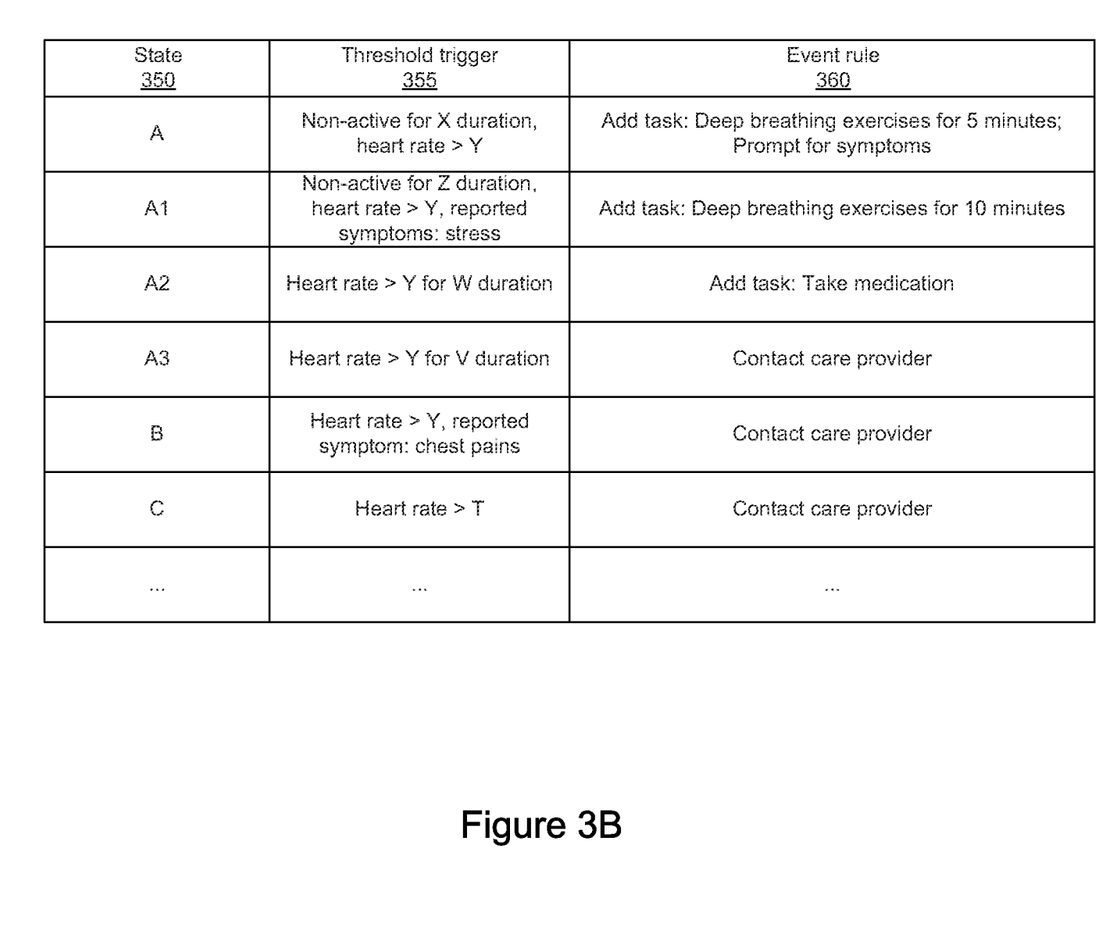
FIG. 3B illustrates a table listing states and associated thresholds and event rules, according to one embodiment.

As the care plan 113 transitions into another state, the care plan management application 111 modifies the care plan 113, e.g., by adding, changing, or removing tasks and thresholds as specified by an event rule 114 associated with the state. FIG. 3B illustrates a table listing states associated with each threshold and event rule, according to one embodiment. As shown, the table includes a state column 350, a threshold triggers column 355, and a event rules column 360. The state column 350 lists the states depicted in FIG. 3A.

The threshold triggers column 355 lists conditions that observed metrics must satisfy to trigger a threshold of a given state. For example, a threshold for state A specifies that the observed metrics should indicate that the patient 103 is currently sedentary and the patient's heart rate is greater than a value Y. If so observed, the care plan 113 transitions from a current state to an A state.

The event rules column 360 lists tasks for the care plan management application 111 to add, remove, or modify to the care plan 113 in response to observed biometrics triggering a threshold. For example, if the observed metrics triggers thresholds associated with state A, then the care plan 113 adds a task instructing the patient to perform deep breathing exercises for five minutes. Added tasks generally aim for reorienting observed metrics towards a desired result. The event rule may also specify that the care plan management application 111 insert new thresholds, e.g., thresholds associated with branching states, to the care plan.

In one embodiment, prior to transitioning to a new state, the care plan management application 111 may require approval from a care provider 101. For example, assume a given event rule specifies a task to be added to the care plan 113 that instructs the patient 103 to take a higher dosage of a given medication. Generally, instructions to alter a prescribed dosage of a given medication (or to change to an entirely different medication) require authorization from the care provider 101. Accordingly, the care plan management application 111 may first notify the care provider 101 of the state change and the proposed task prior to adding the task to the care plan 113. For example, the care plan management application 111 could detect that a particular prescribed medication is not successfully treating a patient's condition, e.g., due to monitored biometric data remaining outside of the target range, due to symptoms reported by the patient, and so on. In response, the care plan management application 111 could generate one or more proposed alterations to the patient's care plan, using rules corresponding to the assigned task as well as the monitored biometric data, reported symptoms and historical treatment information. The care plan management application 111 could transmit these proposed alterations to the care provider 101 and could provide an interface through which the care provider 101 can select and authorize one of the proposed alterations to the patient's care plan. Additionally, the care plan management application 111 could allow the care provider 101 to customize the selected care plan alteration. Once the care plan management application 111 receives authorization for one of the proposed care plan alterations (and any customization of the selected alteration) from the care provider 101 to add the task, the care plan management application 111 adds the task to the care plan 113. Further, in one embodiment, prior to transitioning to a new state, the care plan management application 111 may prompt the care provider 101 to specify tasks to add or to select a task from a list of suggested tasks to add to the care plan 113.

In one embodiment, prior to transitioning to a new state, the care plan management application 111 may evaluate patient information 112 to identify past treatment that was ineffective or adverse to the patient 103 during course of treatment. For example, assume that the patient information 112 indicates that the task of performing light jogging resulted in the reported symptom of knee pain for the patient 103 in the past. If a new state adds a task that instructs the patient 103 to perform light jogging, the care plan management application 111 may avoid adding the task of jogging based on the patient information 112 and could instead substitute a similar low-impact cardiovascular exercise (e.g., walking, use of an elliptical machine, etc.). Alternatively, the care plan management application 111 may notify the care provider 101 of the conflicting task. Thereafter, the care plan management application 111 may receive a customization from the care provider 101 to the care plan 113.

Some states may correspond to end states indicating that added tasks to the care plan 113 are ineffective at improving the patient's biometrics. If the care plan 113 transitions into an end state, then an associated action for the care plan management application 111 may be to contact a care provider or emergency services to further assist the patient. Illustratively, states A3 and C represent end states.

Figure 4:
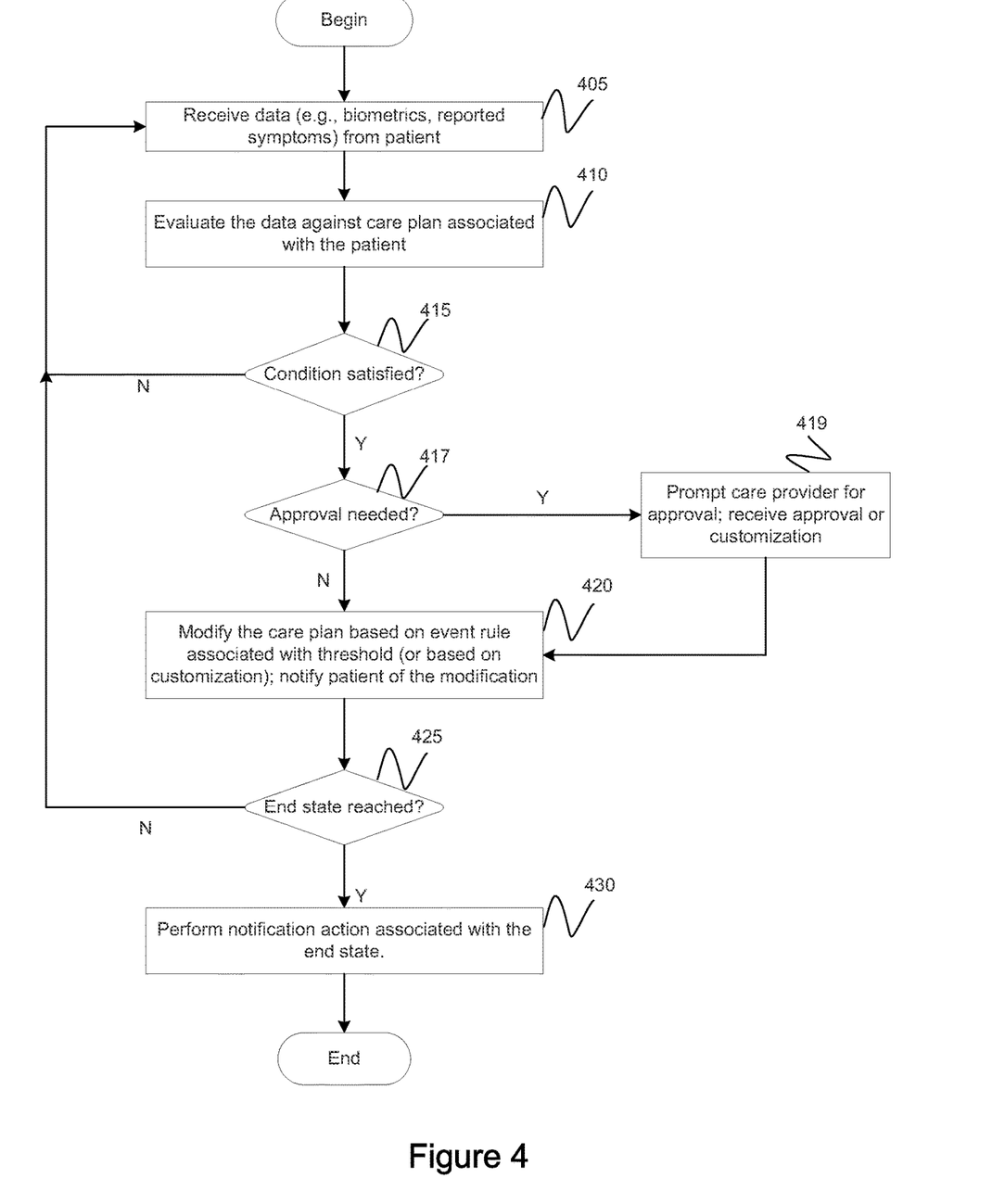
FIG. 4 illustrates a method for modifying a care plan assigned to a patient, according to one embodiment.

FIG. 4 illustrates a method 400 for modifying a care plan assigned to a patient, according to one embodiment. At step 405, the monitoring component 210 receives data from a patient. The data provides biometrics of the patient observed through a variety of sensor devices, such as an adhesive body sensor device, weighing scale, and blood pressure cuff. The observed biometrics may include heart rate, weight, blood pressure, whether the patient is in an active or sedentary state, and so on. In addition, the data can provide symptoms reported to the care plan management application 111 via the patient care application 136, such as whether the patient is experiencing muscle soreness, chills, nausea, and other symptoms unable to be detected by the sensor devices 140.

At step 410, the monitoring component 210 evaluates the sensor data and reported symptoms against the care plan assigned to the patient. The care plan may be targeted towards treating a diagnosed condition of the patient. For example, assume that the care plan is designed to assist the patient in recovery from congestive heart failure. The care plan may include tasks such as performing routine walking exercises, taking prescribed dosages of blood thinning medication at specified intervals, and the like. Further, the care plan may have conditions associated with some of the biometrics and symptoms for detecting potential complications in the patient's adherence to the care plan. For example, some conditions may specify thresholds for the patient's heart rate.

At step 415, the monitoring component 210 determines whether a condition specified in the care plan 113 has been satisfied. If not, then the monitoring component 210 continues to receive sensor data from the patient (at step 405). However, if a given condition is satisfied, then, the event handler component 215 identifies an event rule associated with the condition. If any actions specified in the event rule require care provider approval (at step 417), then, at step 419, the care plan management application 111 notifies a care provider and prompts the care provider for approval for or customizations to the tasks to be added. At step 420, the event handler component 215 performs the actions specified in the event rule (or actions specified by the care provider). Continuing the previous example, assume that the sensor data indicates that the patient's heart rate exceeds the specified threshold. In response, the event handler component 215 identifies the event rule corresponding to the threshold trigger. The event handler component 215 modifies the care plan according to the event rule, e.g., by adding, removing, or changing tasks and thresholds. Doing so effectively transitions the care plan to a state associated with the threshold and the event rule. For example, the event handler component 215 may include an additional task instructing the patient to perform deep breathing exercises or relocate to a stress-free environment so that the patient can reduce heart rate.

At step 425, the event handler component 215 determines whether an end state has been reached. In other words, if the event rule 215 does not provide any further tasks or modifications to be added to the care plan, then an end state has been reached. The event rule may specify an action to be performed as a result of reaching the end state, e.g., alert a care provider or emergency services about the observed metrics. At step 430, the event handler component 215 performs the action. However, if an end state has not been reached, then the monitoring component 210 continues to observe sensor data of the patient (at step 405).

Figure 5:
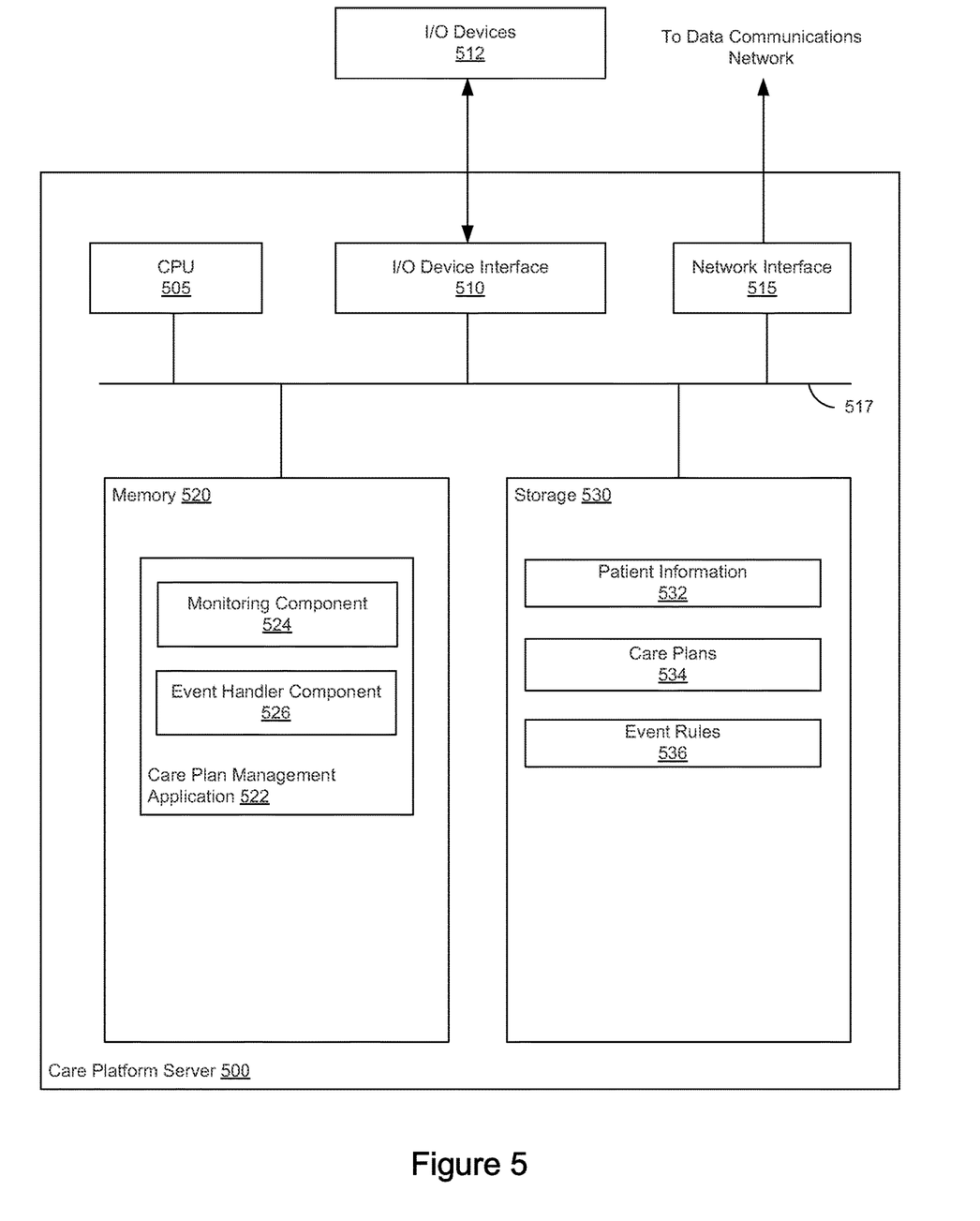
FIG. 5 illustrates a care platform server configured to adjust a care plan based on data observed from a patient, according to one embodiment.

FIG. 5 illustrates a care platform server 500 configured to generate a care plan that may be customized for an individual, according to one embodiment. As shown, the care platform server 500 includes, without limitation, a central processing unit (CPU) 505, a network interface 515, a memory 520, and storage 530, each connected to a bus 517. The care platform server may also include an I/O device interface 510 connecting I/O devices 512 (e.g., keyboard, display and mouse devices) to the care platform server 500. Further, in context of this disclosure, the computing elements shown in the care platform server 500 may correspond to a physical computing system (e.g., a system in a data center) or may be a virtual computing instance executing within a computing cloud.

CPU 505 retrieves and executes programming instructions stored in memory 520 as well as stores and retrieves application data residing in the storage 530. The bus 517 is used to transmit programming instructions and application data between CPU 505, I/O devices interface 510, storage 530, network interface 517, and memory 520. Note, CPU 505 is included to be representative of a single CPU, multiple CPUs, a single CPU having multiple processing cores, and the like. Memory 520 is generally included to be representative of a random access memory. Storage 530 may be a disk drive storage device. Although shown as a single unit, storage 530 may be a combination of fixed and/or removable storage devices, such as fixed disc drives, removable memory cards, or optical storage, network attached storage (NAS), or a storage area-network (SAN).

Illustratively, memory 520 includes a care plan management application 522. And storage 530 includes patient information 532, care plans 534, and event rules 536. The care plan management application 522 further includes a monitoring component 524 and an event handler component 526. The monitoring component 524 receives sensor data sent by a patient (e.g, via an application on the patient's mobile device). The sensor data may include a variety of patient biometrics, such as blood pressure, heart rate, weight, breath rate, calories burned per hour, whether the patient is active or sedentary, etc. The monitoring component 524 evaluates the sensor data against a care plan 534 assigned to a patient.

A care plan 534 is a set of tasks, thresholds, and other metrics targeted towards treating a certain condition (or group of conditions) diagnosed in a patient. Further, the care plan 534 is adaptive, in that the care plan management application 522 may modify the care plan 534 in response to the observed biometrics triggering a care plan threshold.

In one embodiment, when the monitoring component 524 determines that the observed biometrics and/or reported symptoms of a patient satisfies a condition, the monitoring component 524 sends the biometric and threshold data to the event handler component 526. In turn, the event handler component 526 identifies a corresponding event rule 536. Event rules 536 specify actions that the event handler component 526 takes in response to triggering a threshold. Particularly, event rules 536 may specify tasks and thresholds to add, change, or remove from the care plan 536. The event handler component 526 modifies the care plan 536 based on the corresponding event rule 536.

One embodiment of the present disclosure is implemented as a program product for use with a computer system. The program(s) of the program product defines functions of the embodiments (including the methods described herein) and can be contained on a variety of computer-readable storage media. Examples of computer-readable storage media include (i) non-writable storage media (e.g., read-only memory devices within a computer such as CD-ROM or DVD-ROM disks readable by an optical media drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present disclosure, are embodiments of the present disclosure. Other examples media include communications media through which information is conveyed to a computer, such as through a computer or telephone network, including wireless communications networks.

In general, the routines executed to implement the embodiments of the present disclosure may be part of an operating system or a specific application, component, program, module, object, or sequence of instructions. The computer program of the present disclosure is comprised typically of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the disclosure. However, it should be appreciated that any particular program nomenclature that follows is used merely for convenience, and thus the present disclosure should not be limited to use solely in any specific application identified and/or implied by such nomenclature.

As described, embodiments herein provide techniques for automatically modifying a care plan in response to observed patient metrics, such as weight, blood pressure, heart rate, and reported symptoms. The care platform monitors patient activity and detects instances where patient metrics deviate from expected values or exceed specified thresholds. The care plan automatically adjusts the care plan in response to the deviation by adding tasks, thresholds, and other information targeted to guiding the patient metrics to a desired state. Advantageously, embodiments presented herein provide an adaptive care plan that is responsive to sensor data sent by a patient associated with the care plan.

While the foregoing is directed to embodiments of the present disclosure, other and further embodiments of the disclosure may be devised without departing from the basic scope thereof, and the scope thereof is determined by the claims that follow.

What is claimed is:

1. A method for modifying a care plan assigned to a patient in response to data observed from the patient, the method comprising:
    retrieving the care plan from a computer storage at a server, wherein the care plan comprises a plurality of care plan protocols, each care plan protocol addressing a respective medical condition of the patient and comprising: (i) a biometric threshold related to biometric data for the patient and (ii) a treatment action for the patient related to the medical condition;
    transmitting the care plan from the server to a mobile device associated with the patient and storing the care plan at the mobile device,
    wherein the mobile device is configured to provide the treatment actions associated with each care plan protocol in the care plan to the patient, based on the care plan,
    wherein the mobile device is configured to parse the received care plan to identify a first biometric threshold of the biometric thresholds in the care plan, and
    wherein the mobile device is configured to configure logic on one or more remote biometric sensor devices to monitor biometric data for the patient and determine whether the first biometric threshold is exceeded;
    receiving data at the server from the one or more biometric sensor devices using the mobile device, the data corresponding to the biometric data for the patient, wherein the data corresponds with at least one of the biometric thresholds in the care plan;
    dynamically modifying the care plan, at the server, based on the received data, the modifying comprising:
        identifying a plurality of states relating to the care plan, each state comprising a threshold trigger and an event rule;
    determining a current state of the care plan, of the plurality of states;
        selecting a next state for the care plan, of the plurality of states, based on the current state and the received data, wherein the next state comprises a next threshold trigger and a next event rule, and wherein the selecting comprises determining that the received data satisfies the next threshold trigger of the next state;
    modifying the care plan based on the next event rule of the next state, wherein the modified care plan specifies one or more remedial actions related to treatment for the patient; and
    transitioning the care plan from the current state to the next state;
        transmitting the modified care plan from the server to the mobile device associated with the patient, wherein the mobile device is configured to store the modified care plan, and wherein the mobile device is configured to provide the one or more remedial actions to the patient, based on the modified care plan; and
    storing the modified care plan at the server in the computer storage.

2. The method of claim 1, wherein the next event rule specifies the one or more remedial actions and one or more additional conditions to add to the care plan, and wherein modifying the care plan comprises, adding the one or more remedial actions and conditions to the care plan.

3. The method of claim 2, further comprising:
    upon determining that subsequently observed biometric data satisfies one or more of the additional conditions, identifying an additional event rule corresponding to the satisfied additional conditions.

4. The method of claim 3, wherein the additional event rule corresponding to the satisfied additional conditions specifies a care provider to contact.

5. The method of claim 1, further comprising, notifying the patient of the modification to the care plan.

6. The method of claim 1, wherein the biometric data includes at least one of a blood pressure measure, a weight measure, or a heart rate measure of a patient.

7. The method of claim 1, wherein the one or more remedial actions relate to a treatment action the patient and wherein the mobile device is configured to provide the treatment action to the patient based on the care plan.

8. The method of claim 1, further comprising:
    determining, at the server, that the event rule requires authorization prior to modifying the care plan;
    identifying a care provider associated with the patient to provide authorization;
    prompting the care provider for authorization; and
    determining that the care provider has authorized modifying the care plan.

9. The method of claim 1, wherein the server receives the data from the one or more biometric sensor devices via the mobile device, and wherein the server receives one or more reported symptoms from the mobile device.

10. The method of claim 1, further comprising:
    generating a plurality of event rules for the plurality of states relating to the care plan, based a treatment history for the patient, wherein the generating comprises:
    identifying at least one beneficial previous treatment with a beneficial effect toward the patient and generating a first event rule related to the beneficial previous treatment; and
    identifying at least one adverse previous treatment with an adverse effect toward the patient, and adjusting the care plan based on the adverse previous treatment.

11. A computer-readable storage medium storing instructions, which, when executed on a processor, performs an operation for modifying a care plan assigned to a patient in response to data observed from the patient, the operation comprising:
    retrieving the care plan from a computer storage at a server, wherein the care plan comprises a plurality of care plan protocols, each care plan protocol addressing a respective medical condition of the patient and comprising: (i) a biometric threshold related to biometric data for the patient and (ii) a treatment action for the patient related to the medical condition;
    transmitting the care plan from the server to a mobile device associated with the patient and storing the care plan at the mobile device,
    wherein the mobile device is configured to provide the treatment actions associated with each care plan protocol in the care plan to the patient, based on the care plan,
    wherein the mobile device is configured to parse the received care plan to identify a first biometric threshold of the biometric thresholds in the care plan, and
    wherein the mobile device is configured to configure logic on one or more remote biometric sensor devices to monitor biometric data for the patient and determine whether the first biometric threshold is exceeded;

receiving data at the server from the one or more biometric sensor devices using the mobile device, the data corresponding to the biometric data for the patient, wherein the data corresponds with at least one of the biometric thresholds in the care plan;

dynamically modifying the care plan, at the server, based on the received data, the modifying comprising:

identifying a plurality of states relating to the care plan, each state comprising a threshold trigger and an event rule;

determining a current state of the care plan, of the plurality of states;

selecting a next state for the care plan, of the plurality of states, based on the current state and the received data, wherein the next state comprises a next threshold trigger and a next event rule, and wherein the selecting comprises determining that the received data satisfies the next threshold trigger of the next state;

modifying the care plan based on the next event rule of the next state, wherein the modified care plan specifies one or more remedial actions related to treatment for the patient; and transitioning the care plan from the current state to the next state;

transmitting the modified care plan from the server to the mobile device associated with the patient, wherein the mobile device is configured to store the modified care plan, and wherein the mobile device is configured to provide the one or more remedial actions to the patient, based on the modified care plan; and storing the modified care plan at the server in the computer storage.

12. The computer-readable storage medium of claim 11, wherein the next event rule specifies the one or more remedial actions and one or more additional conditions to add to the care plan, and wherein modifying the care plan comprises, adding the one or more remedial actions and conditions to the care plan, and wherein the operation further comprises:

upon determining that subsequently observed biometric data satisfies one or more of the additional conditions, identifying an additional event rule corresponding to the satisfied additional conditions.

13. The computer-readable storage medium of claim 12, wherein the additional event rule corresponding to the satisfied additional conditions specifies a care provider to contact.

14. The computer-readable storage medium of claim 11, wherein the next event rule specifies one or more tasks to remove from the care plan, and wherein modifying the care plan comprises, removing the one or more tasks from the care plan.

15. The computer-readable storage medium of claim 11, the operation further comprising:

generating a plurality of event rules for the plurality of states relating to the care plan, based a treatment history for the patient, wherein the generating comprises:

identifying at least one beneficial previous treatment with a beneficial effect toward the patient and generating a first event rule related to the beneficial previous treatment; and identifying at least one adverse previous treatment with an adverse effect toward the patient, and adjusting the care plan based on the adverse previous treatment.

16. A system, comprising:

a processor; and a memory storing one or more application programs, which, when executed on the processor, are configured to perform an operation modifying a care plan assigned to a patient in response to data observed from the patient, the operation comprising:

retrieving the care plan from a computer storage at a server, wherein the care plan comprises a plurality of care plan protocols, each care plan protocol addressing a respective medical condition of the patient and comprising: (i) a biometric threshold related to biometric data for the patient and (ii) a treatment action for the patient related to the medical condition;

transmitting the care plan from the server to a mobile device associated with the patient and storing the care plan at the mobile device, wherein the mobile device is configured to provide the treatment actions associated with each care plan protocol in the care plan to the patient, based on the care plan, wherein the mobile device is configured to parse the received care plan to identify a first biometric threshold of the biometric thresholds in the care plan, and wherein the mobile device is configured to configure logic on one or more remote biometric sensor devices to monitor biometric data for the patient and determine whether the first biometric threshold is exceeded;

receiving data at the server from the one or more biometric sensor devices using the mobile device, the data corresponding to the biometric data for the patient, wherein the data corresponds with at least one of the biometric thresholds in the care plan;

dynamically modifying the care plan, at the server, based on the received data, the modifying comprising:

identifying a plurality of states relating to the care plan, each state comprising a threshold trigger and an event rule;

determining a current state of the care plan, of the plurality of states;

selecting a next state for the care plan, of the plurality of states, based on the current state and the received data, wherein the next state comprises a next threshold trigger and a next event rule, and wherein the selecting comprises determining that the received data satisfies the next threshold trigger of the next state;

modifying the care plan based on the next event rule of the next state, wherein the modified care plan specifies one or more remedial actions related to treatment for the patient; and transitioning the care plan from the current state to the next state;

transmitting the modified care plan from the server to the mobile device associated with the patient, wherein the mobile device is configured to store the modified care plan, and wherein the mobile device is configured to provide the one or more remedial actions to the patient, based on the modified care plan; and storing the modified care plan at the server in the computer storage.

17. The system of claim 16, wherein the next event rule specifies the one or more remedial actions and one or more additional conditions to add to the care plan, and wherein modifying the care plan comprises, adding the one or more remedial actions and conditions to the care plan, and wherein the operation further comprises:
upon determining that subsequently observed biometric data satisfies one or more of the additional conditions, identifying an additional event rule corresponding to the satisfied additional conditions.

18. The system of claim 17, wherein the additional event rule corresponding to the satisfied additional conditions specifies a care provider to contact.

19. The system of claim 16, wherein the biometric data includes at least one of a blood pressure measure, a weight measure, or a heart rate measure of a patient.

20. The system of claim 16, the operation further comprising:
generating a plurality of event rules for the plurality of states relating to the care plan, based a treatment history for the patient, wherein the generating comprises:
identifying at least one beneficial previous treatment with a beneficial effect toward the patient and generating a first event rule related to the beneficial previous treatment; and
identifying at least one adverse previous treatment with an adverse effect toward the patient, and adjusting the care plan based on the adverse previous treatment.

* * * * *